United States Patent [19]

Watson et al.

[11] 4,185,498
[45] Jan. 29, 1980

[54] FLOWMETER

[75] Inventors: Christopher A. Watson, Upland, Calif.; Kenneth E. Bearcroft, Bishop's Stortford, England; Michael Bronzite, Brussels, Belgium; Alan G. Palmer, Hertford, England

[73] Assignee: ITT Industries, Inc., New York, N.Y.

[21] Appl. No.: 926,260

[22] Filed: Jul. 20, 1978

[30] Foreign Application Priority Data

Jun. 3, 1977 [GB] United Kingdom ............... 23787/77

[51] Int. Cl.² ................................................ G01F 1/66
[52] U.S. Cl. ...................................... 73/194 A; 73/597
[58] Field of Search ............................... 73/194 A, 597

[56] References Cited

U.S. PATENT DOCUMENTS

| 3,697,936 | 10/1972 | Zacharins, Jr. et al. ...... 73/194 A X |
| 3,818,757 | 6/1974 | Brown .................................. 73/194 A |
| 3,894,431 | 7/1975 | Muston et al. ..................... 73/194 A |
| 4,069,713 | 1/1978 | Gassmann ........................... 73/194 A |
| 4,114,439 | 9/1978 | Fick .................................... 73/194 A |

Primary Examiner—Charles A. Ruehl
Attorney, Agent, or Firm—A. Donald Stolzy

[57] ABSTRACT

A flowmeter sometimes called ultrasonic, but sometimes not ultrasonic including two phase locked loops, a portion of each of which form a common path through amplifiers, an electronic attenuator with automatic gain control, a pulse detector, and a pulse or phase comparator. The pulse comparator, through switches, controls first and second voltage controlled oscillators on a time shared basis. First and second counters are connected from the first and second voltage controlled oscillators, respectively. The first and second counters supply transmission pulses to submerged first and second facing transducers, respectively, at different times. The voltage controlled oscillators are always driven until a later counter pulse coincides with a corresponding received pulse. Time sharing is, in part, accomplished by beginning energy propagation in opposite directions at successive times and before either pulse is received.

9 Claims, 13 Drawing Figures

SWITCHING CIRCUIT 23

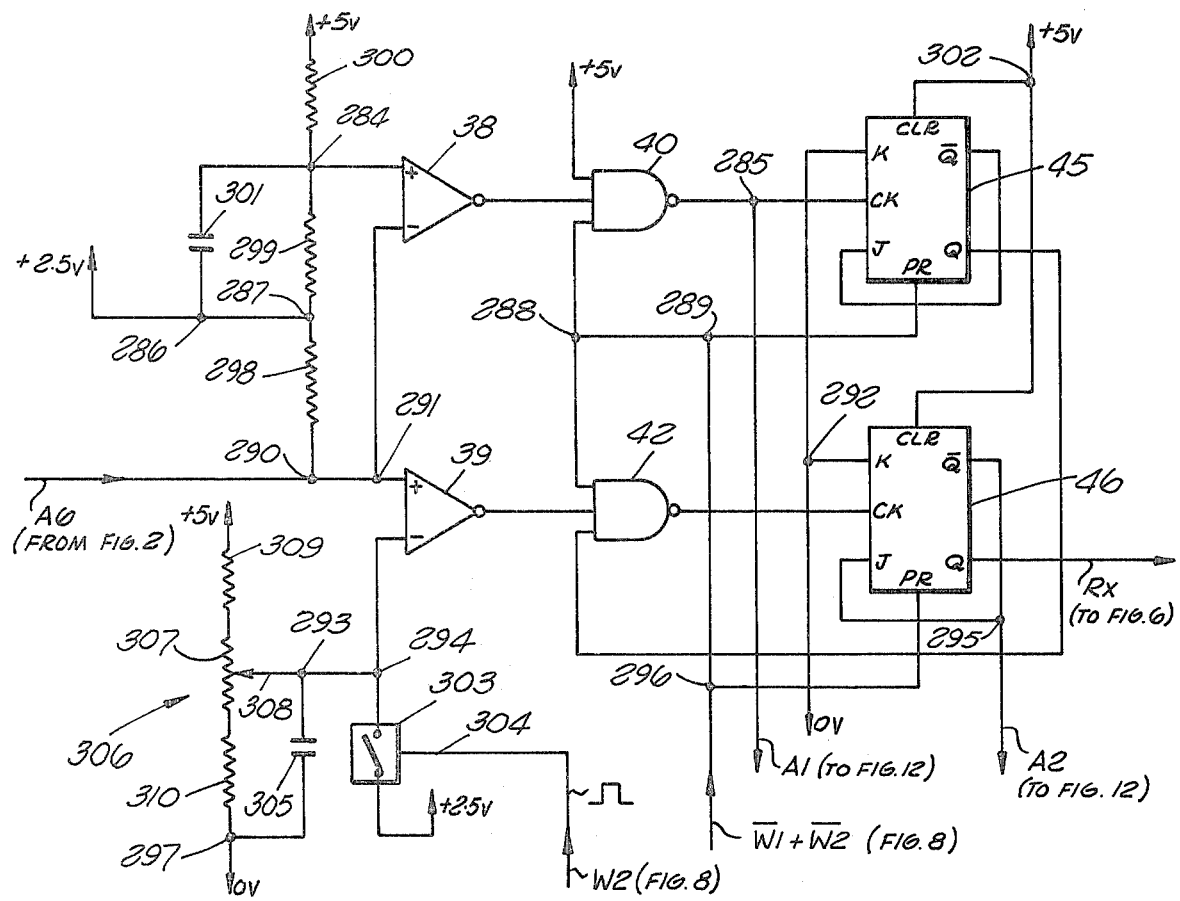
FIG. 4 PULSE DETECTOR 30
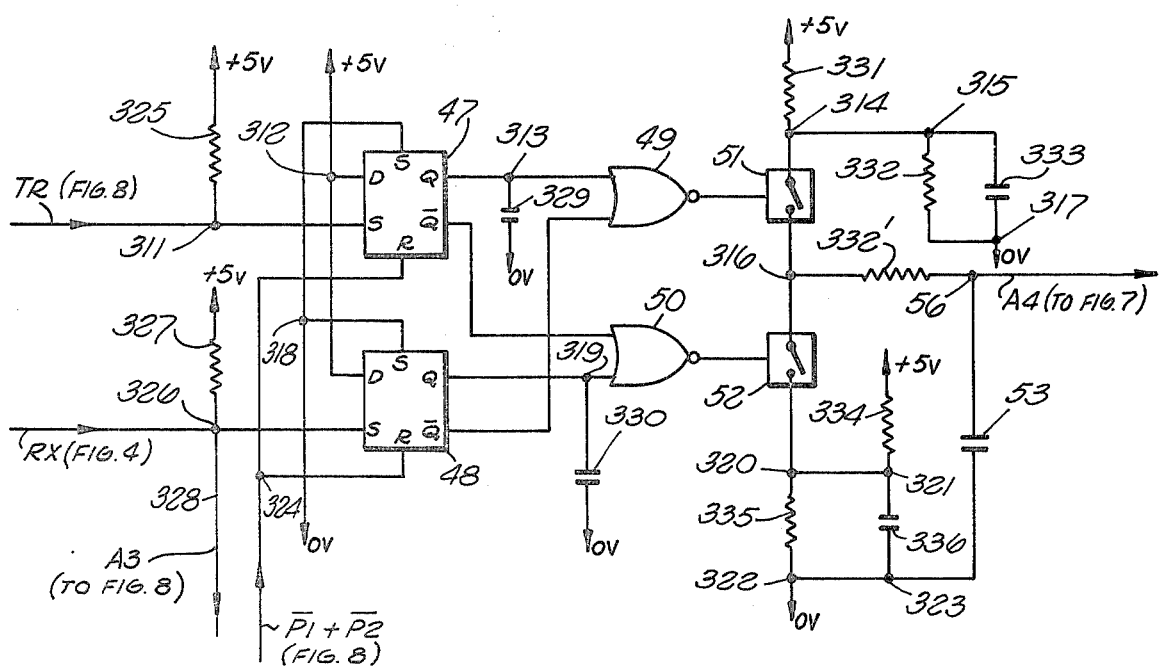
FIG. 6 PULSE COMPARATOR 31

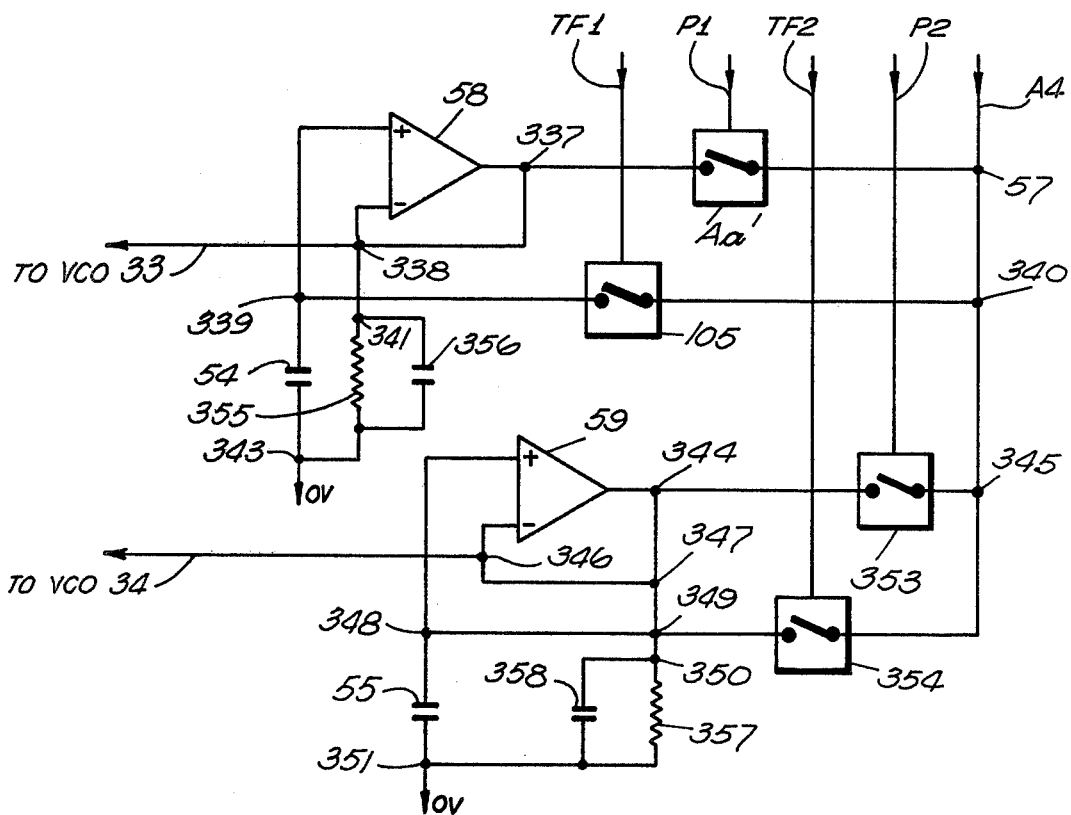
FIG. 7 CHARGE STORAGE CIRCUIT 32
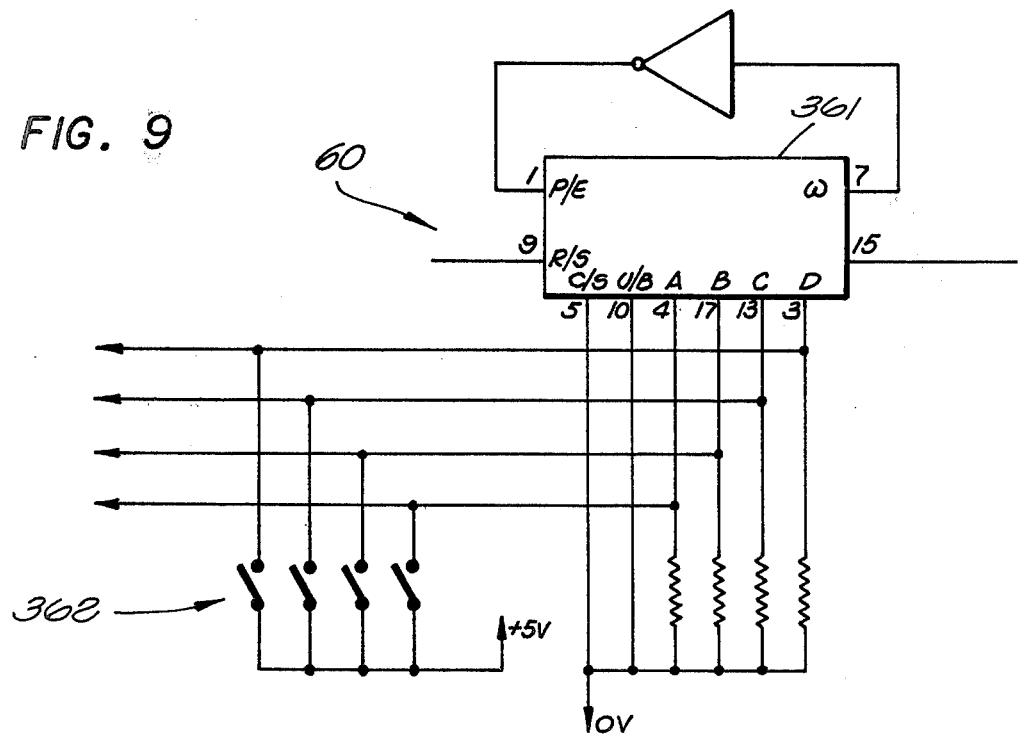
FIG. 9

TIMING CIRCUIT 35

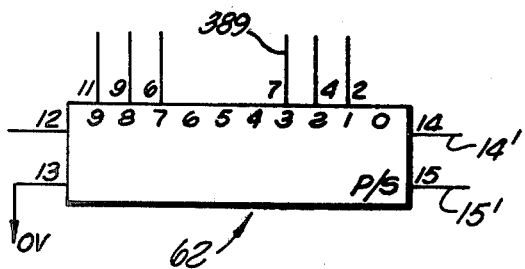
FIG. 10
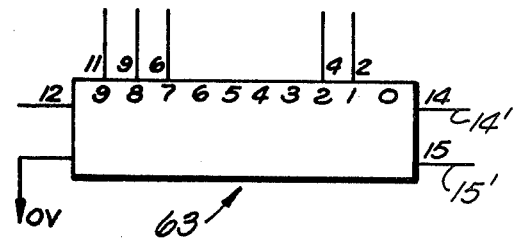
FIG. 11
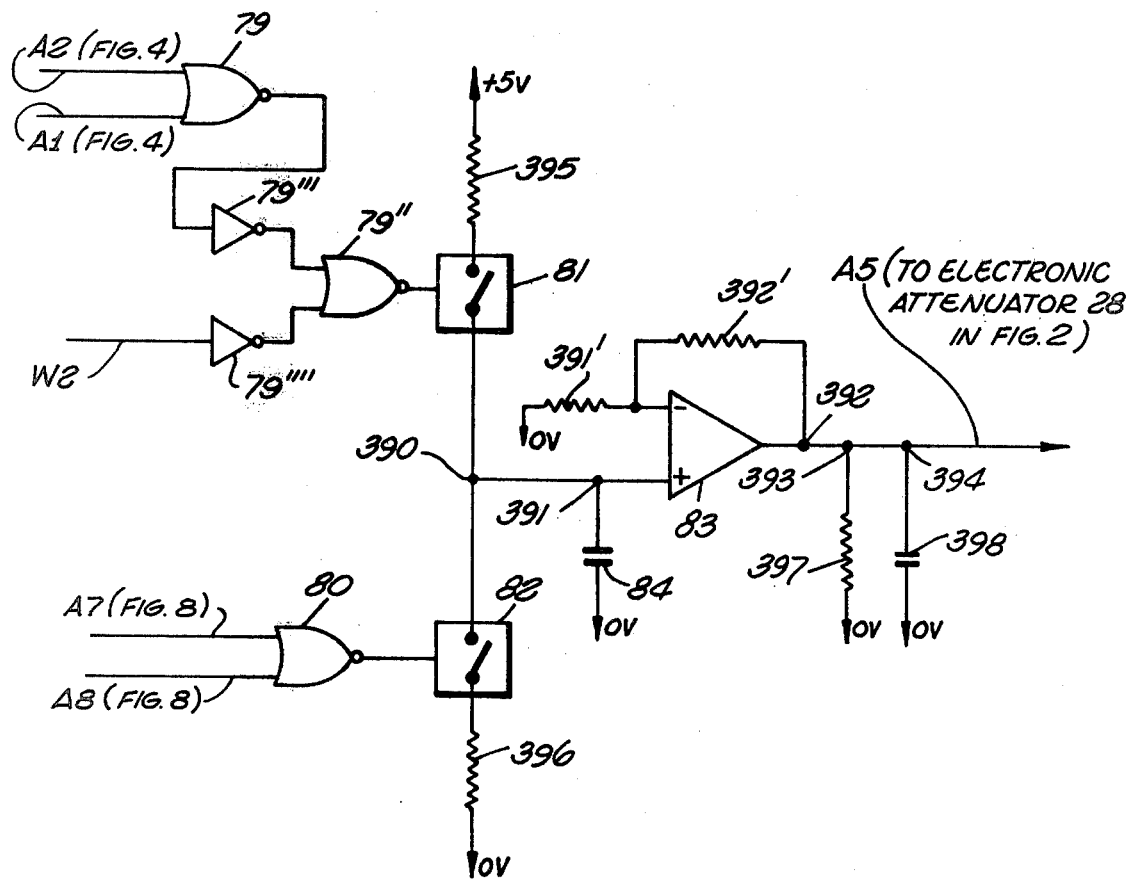
FIG. 12 AGC CIRCUIT 36

FLOWMETER

BACKGROUND OF THE INVENTION

This invention pertains to a fluid property detector in which pulses are alternately transmitted upstream and downstream, and more particularly to apparatus in which the output frequencies of two voltage controlled oscillators are varied in a manner to keep transit times in opposite directions between a pair of transducers equal to integral multiples of the output pulses of corresponding oscillators.

PRIOR ART STATEMENT

There is considerable art prior to the present invention, much of which will be found in Subclass 194A, Class 73 of the United States Patent and Trademark Office Manual of Classification.

Perhaps more pertinent prior art includes U.S. Pat. No. 4,069,713 issued Jan. 24, 1978, in which two voltage controlled oscillators are employed.

SUMMARY OF THE INVENTION

According to one aspect of the present invention, there is provided a flowmeter comprising: a first transducer for mounting at a first point in a pipeline; a second transducer for mounting in alignment with said first transducer, but at a second point in said pipeline spaced lengthwise from said first point; first means including first and second voltage controlled oscillators to energize respectively said first and second transducers at first and second respective times to propagate pulses through fluid in said pipeline in opposite directions; second means to receive pulses transmitted from said first and second transducers through said fluid and subsequently through said second and first transducers, respectively; a first threshold detector of one polarity and of a first threshold level connected from said second means; a first storage device; a second storage device having an output lead, said first storage device being adapted to enable and to disable said second storage device, said first storage device being connected from said first threshold detector to enable said second storage device when said first threshold level is exceeded; a second threshold detector of a polarity opposite said one polarity and of a second threshold level connected from said second means to said second storage device to transmit a received pulse from said second storage device on said output lead thereof when said second threshold level is reached, but only after said first storage device has enabled said second storage device; third means operable synchronously with said first means to reset said first and second storage devices; and fourth means connected from said second storage device output lead to said first and second voltage controlled oscillators to maintain the difference between the output frequencies of said first and second voltage controlled oscillators directly proportional to one condition of a fluid in the pipeline.

According to another aspect of the present invention, there is provided a flowmeter comprising: a first transducer for mounting at a first point in a pipeline; a second transducer for mounting in alignment with said first transducer, but at a second point in said pipeline spaced lengthwise from said first point; first means including first and second voltage controlled oscillators to energize respectively said first and second transducers at first and second respective times to transmit vibrations through fluid in said pipeline in opposite directions; second means to receive vibrations transmitted from said first and second transducers through said fluid and subsequently through said second and first transducers, respectively; a first counter adapted to count a plurality of pulses before reset, and connected from said first voltage controlled oscillator (VCO); a second counter adapted to count a plurality of pulses before reset, and connected from said second VCO; third means connected from said second means and said first and second counters to control the frequency of said first VCO and to control the frequency of said second VCO in a manner such that a first pulse, transmitted at a first time by said first transducer, arrives at said second transducer a second time later than said first time by an integral number of counts of said first counter, and in a manner such that a third pulse, transmitted at a third time by said second transducer, arrives at said first transducer a fourth time later than said third time by an integral number of counts of said second counter.

According to still another aspect of the present invention, there is provided a flowmeter comprising: a first transducer for mounting at a first point in a pipeline; a second transducer for mounting in alignment with said first transducer, but at a second point in said pipeline spaced lengthwise from said first point; first means including first and second voltage controlled oscillators to energize respectively said first and second transducers at first and second respective times to transmit vibrations through fluid in said pipeline in opposite directions; second means to receive vibrations transmitted from said first and second transducers through said fluid and subsequently through said second and first transducers, respectively; a time shared comparator having an output capacitor and third means to charge and to discharge said output capacitor when one received pulse arrives respectively after and before a corresponding pulse of the output of a voltage controlled oscillator (VCO) which caused the transmission of the pulse received; first and second storage capacitors to provide input control voltages to said first and second VCO's, respectively; and first and second switches connected from said output capacitor to said first and second storage capacitors, respectively; and fourth means connected from said first and second VCO's to operate each of said first and second switches momentarily, respectively, to modify the charge on said first and second storage capacitors when necessary to change the VCO frequencies such that the said received pulses occur after an integral number of pulses of a corresponding VCO.

According to still a further aspect of the present invention, there is provided a compound phase locked loop for detecting a property of a fluid comprising: a first voltage controlled oscillator (VCO) having an input and an output; a second VCO having an input and an output; a first transducer; a second transducer, said first and second transducers each being adapted to transmit and to receive energy respectively to and from each other, the transit times of the propagation of energy from said first transducer to said second transducer and vice versa being a function of the acoustical velocity and volume rate of flow of a fluid located between said first and second transducers; logic means connected from the outputs of both of said VCO's to sequence operation, said logic means including first counter means connected from said first VCO to transmit first pulses only from said first transducer on a count of said first counter means, said logic means including second counter means connected from said second VCO to transmit second pulses from said second transducer on a count of said second counter means, but spaced in time from said first pulses and all received pulses; a common receiver to act upon pulses received by both of said transducers, said common receiver producing received pulse edges; a common pulse comparator connected from both of said VCO's and from said common receiver to receive pulse edges therefrom, said logic means including third means to supply pulse edges for comparison from said first and second counter means to said common pulse comparator; first and second electronic servo means connected from said common pulse comparator to said first and second VCO inputs, respectively, and actuable to cause a first alternate set of received pulse edges to lie in coincidence with edges corresponding to output pulses of said first counter means, and actuable to cause a second alternate set of said received pulse edges to lie in coincidence with edges corresponding to output pulses of said second counter means; and first and second switch means to connect said comparator to said VCO inputs alternately on a time shared basis.

According to another aspect of the invention, there is provided a phase locked loop comprising: a voltage controlled oscillator (VCO) having an input and an output; a pulse comparator having first and second inputs and an output; means connected from said VCO output to transmit a pulse over a path which varies the propagation time, said transmitted pulse being received at the end of said path by said pulse comparator first input, said pulse comparator second input being connected from said VCO output, said comparator output being connected to said VCO input to act as an electronic servomechanism and to drive said VCO until the output thereof produces a predetermined number of integral cycles during the time period between the instant that said pulse is transmitted and the instant that it is received at said pulse comparator first input, said pulse comparator including a first capacitor to retain a voltage to drive said VCO, a second capacitor having a capacitance smaller than said first capacitor, first means actuable to charge said second capacitor periodically to the voltage of said first capacitor, second means actuable to charge or to discharge said second capacitor depending upon the accuracy of the number and phase of said predetermined number of cycles, third means actuable to connect said first and second capacitors in parallel for equalizing the voltages thereon, and fourth means to actuate said first means, said second means, and said third means repeatedly in that order.

BRIEF DESCRIPTION OF THE DRAWINGS

In the accompanying drawings which illustrate exemplary embodiments of the present invention:

FIG. 4 is a schematic diagram of a pulse detector shown in FIG. 2;

FIG. 6 is a schematic diagram of a pulse comparator shown in FIG. 2;

FIG. 7 is a schematic diagram of a charge storage circuit shown in FIG. 2;

FIGS. 9, 10 and 11 are enlarged views of dividers and counters shown in FIG. 8;

FIG. 12 is a schematic diagram of an AGC circuit shown in FIG. 2; and

DESCRIPTION OF THE PREFERRED EMBODIMENT

Figure 1:
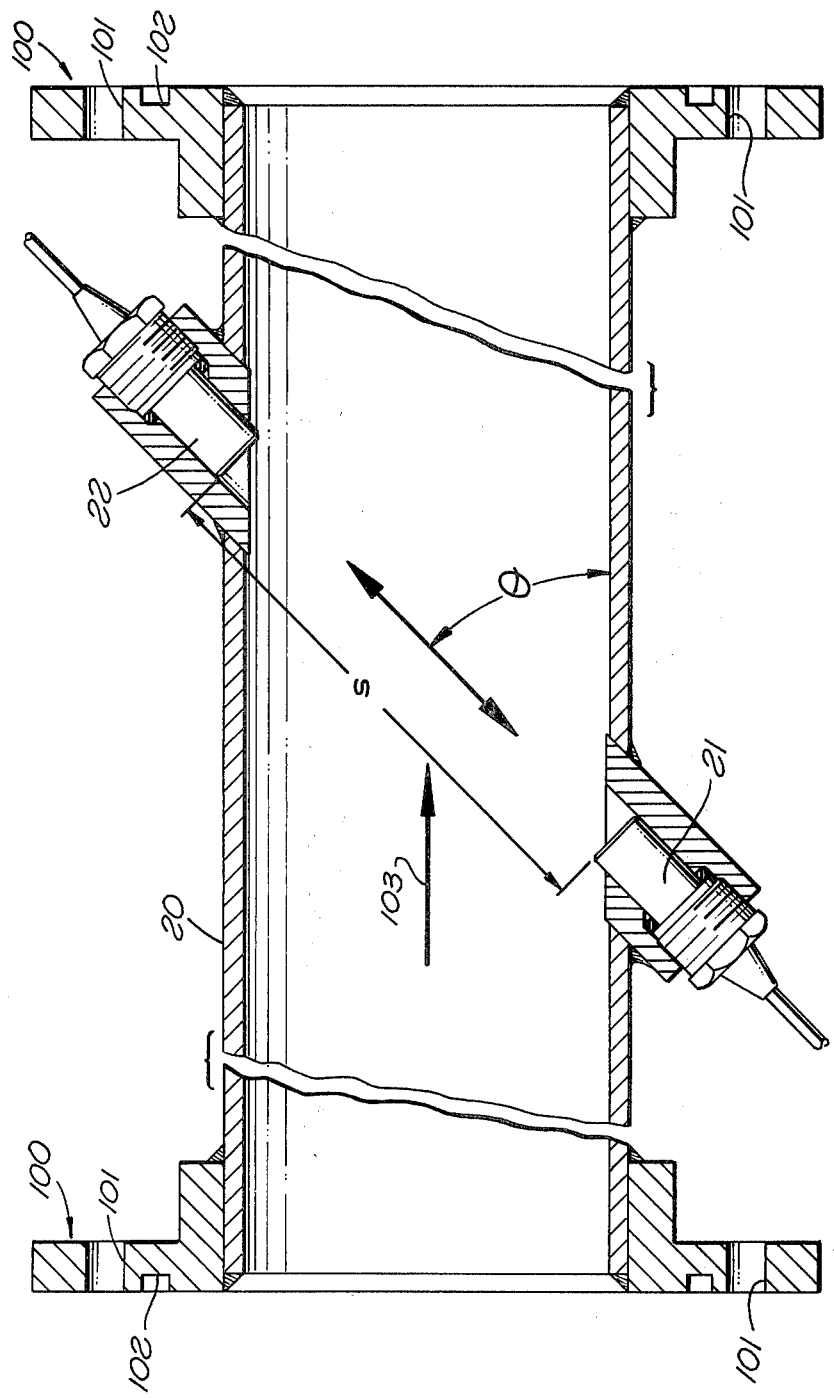
FIG. 1 is a longitudinal sectional view, partly in elevation, of a portion of a flowmeter constructed in accordance with the present invention.

A pipe section 20 is shown in FIG. 1 having transducers 21 and 22 mounted therein to transmit vibrations toward each other, and to receive the vibrations. The arrangement in FIG. 1 may be entirely conventional.

Flanges 100 with bolt holes 101 and O-ring grooves 102 may be fixed to pipe section 20 for attachment in a pipeline.

Figure 2:
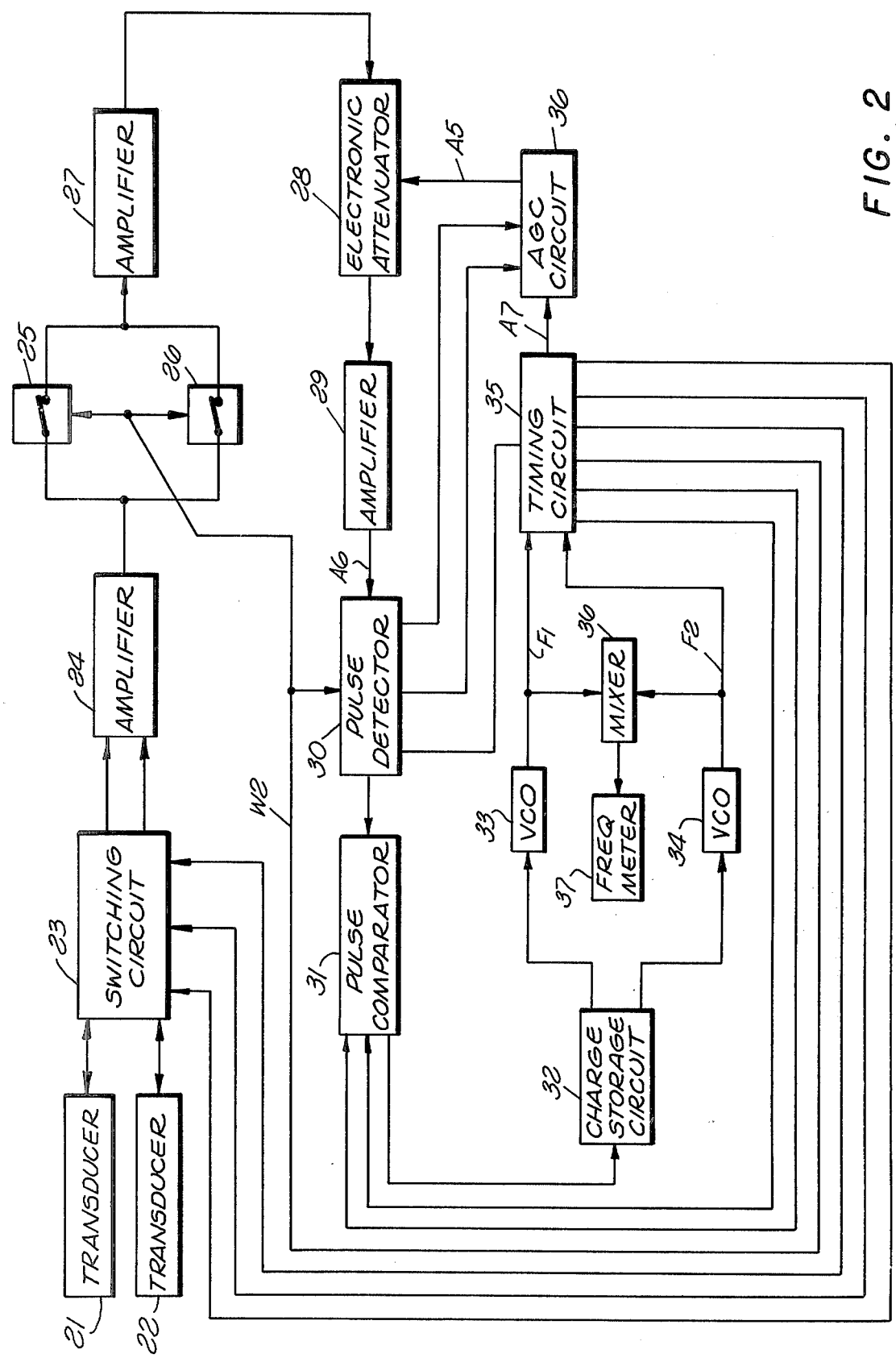
FIG. 2 is a block diagram of the flowmeter of the present invention.

In FIG. 2, transducers 21 and 22 are shown connected to a switching circuit 23.

The output of circuit 23 is impressed upon an amplifier 24 which passes through electronic switches 25 or 26 to an amplifier 27. Amplifier 24 and switches 25 and 26 may be conventional—single chip (integrated circuit) Motorola MC1445.

The output of amplifier 27 passes through an electronic attenuator 28 and thence through an amplifier 29 to a pulse detector 30.

Electronic attenuator 28 is entirely conventional and is model MC3340P (Motorola).

The output of pulse detector 30 is impressed upon a pulse comparator 31 and thence through a charge storage circuit 32 and a voltage controlled oscillator (VCO) 33. Circuit 32 also has an output connected to an input of a VCO 34.

The outputs of VCO's 33 and 34 are impressed upon a timing circuit 35 and also upon a mixer 36 connected to a frequency meter 37 that may be calibrated in volume rate of flow through pipe section 20 shown in FIG. 1. Timing circuit 35 has an output W2 which is impressed upon pulse detector 30 and switches 25 and 26. An AGC circuit 36 receives an input from circuit 35, and two inputs from detector 30, and provides an output A5 to electronic attenuator 28. The signal received by circuit 36 from circuit 35 is A7. The outputs of VCO's 33 and 34 are F1 and F2, respectively.

Timing circuit 35 provides three inputs to switching circuit 23. Timing circuit 35 also provides an input to pulse detector 30. The output of amplifier 29 to pulse detector 30 is A6. Pulse comparator 31 has an input to charge storage circuit 32 and two inputs from timing circuit 35.

The invention, as shown in FIG. 2, actually includes two phase-locked loops, a portion of one path being common with the other. For example, transducers 21 and 22 are used both to transmit and to receive alternately. Further, the path from amplifier 27 to pulse comparator 31 is common although it is used for each of the VCO's 33 and 34 on a time shared basis.

In FIG. 2, amplifier 24, switches 25 and 26, amplifier 27, electronic attenuator 28 and amplifier 29 may be entirely conventional.

Figure 3:
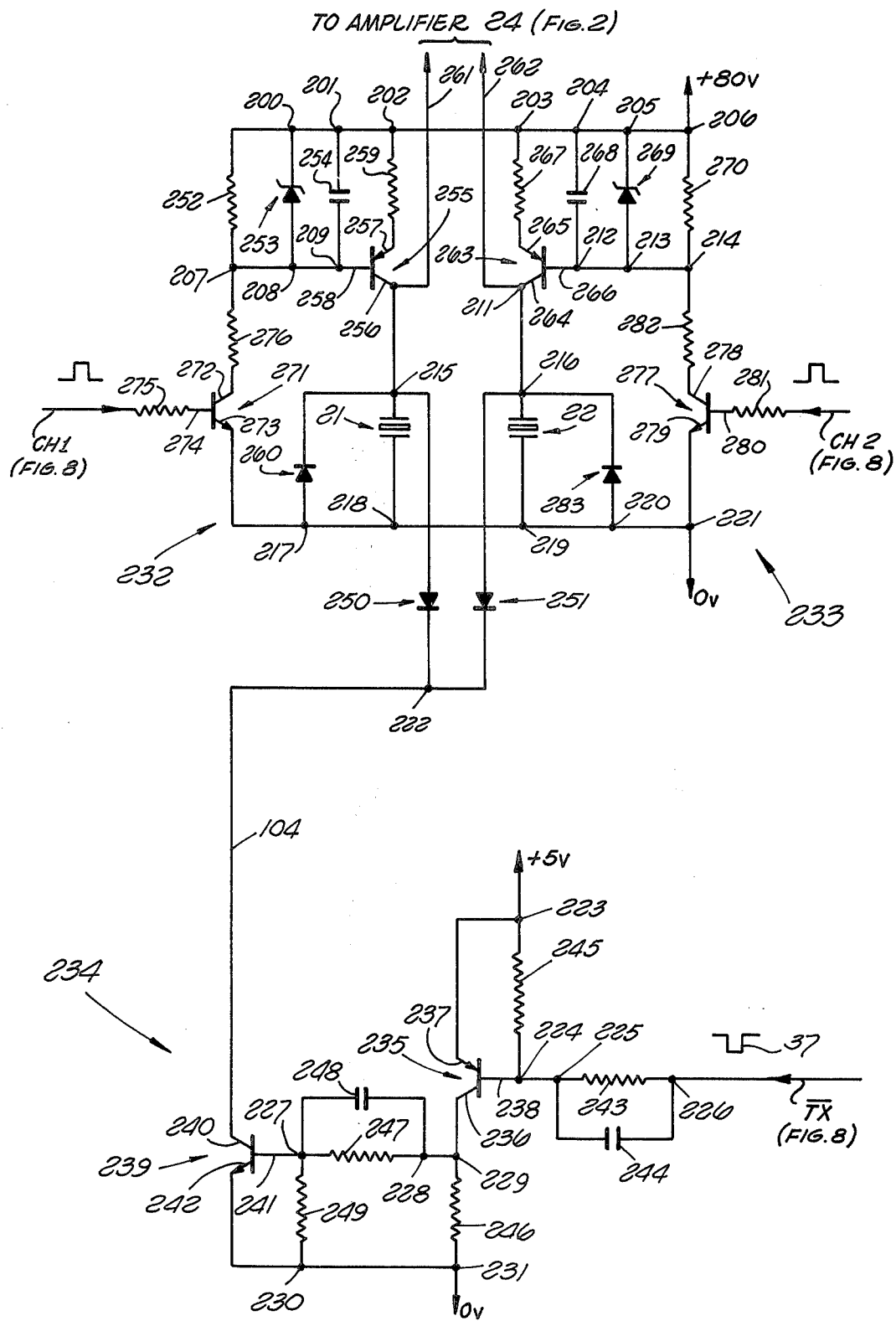
FIG. 3 is a schematic diagram of a switching circuit shown in FIG. 2.

Switching circuit 23 is shown in FIG. 3. A transmit pulse $\overline{TX}$ provided at 37 causes only one of the two transducers 21 and 22 to transmit at one time. Circuit 23 receives two other pulses CH1 and CH2. Transducers 21 and 22 are respectively charged up by pulses CH1 and CH2. Transducers 21 and 22 act like capacitors and may be crystal transducers. Energy release occurs on transducer discharge. Transit time in FIG. 1 from transducer 21 to transducer 22 determines a higher VCO frequency (e.g. F2) if arrow 103 is in the direction of flow. F2 is determined when a pulse is transmitted from transducer 21 to transducer 22. There is a common discharge path of transducers 21 and 22 in FIG. 3, however only one pulse is transmitted because CH1 charges transducer 21 immediately after transducer 22 has been discharged and vice versa. Thus, the next discharge of transducer 21 has no substantial effect on transducer 22 because transducer 22 has been more or less fully discharged and is not charged by CH2 until transducer 21 has been discharged by TX1. In Boolean algebra, TX=TX1+TX2 (see FIG. 13). "TX" means transmitted pulses.

The said common discharge path is indicated at 104 in FIG. 3.

In FIG. 3, junctions are provided at 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230 and 231.

In general, the circuit of FIG. 3 may be divided into three parts. One part includes a charging circuit 232 for transducer 21. The second is a charging circuit 233 for transducer 22. The third is a discharging circuit 234 for both transducers 21 and 22. However, only one of the transducers 21 and 22 is discharged at one time. The inverted input pulses $\overline{TX}$ are applied to junction 226. A PNP transistor is provided at 235 having a collector 236, an emitter 237 and a base 238. Emitter 237 is connected to junction 223 which is maintained at a potential of, for example, 5 volts. Junctions 224 and 225 are connected to base 238. Collector 236 is connected to junction 229. Junctions 228 and 229 are connected together. Another transistor 239 is provided having a collector 240, a base 241 and an emitter 242. Emitter 242 is connected to junction 230. Junctions 230 and 231 are connected, for example, to 0 volts. Collector 240 is connected to junction 222. A resistor 243 and a capacitor 244 are connected in parallel between junctions 225 and 226. A resistor 245 is connected between junctions 223 and 224. A resistor 246 is connected between junctions 229 and 231. A resistor 247 and a capacitor 248 are connected in parallel between junctions 227 and 228. Junction 227 is connected to base 241 of transistor 239. A resistor 249 is connected between junctions 227 and 230.

Diodes 250 and 251 are connected respectively from junctions 215 and 216 to junction 222, and poled to be conductive toward junction 222. Junctions 200, 201, 202, 203, 204, 205 and 206 are connected together and may be maintained at, for example, 80 volts.

Junctions 217, 218, 219, 220 and 221 are all connected together and may be maintained at a potential of, for example, 0 volts. A resistor 252 is connected between junctions 200 and 207. A zener diode 253 is connected between junctions 200 and 208. A capacitor 254 is connected between junctions 201 and 209. A PNP transistor 255 is provided having a collector 256, an emitter 257 and a base 258. Junctions 207, 208 and 209 are connected to base 258. A resistor 259 is connected between junction 202 and emitter 257. Collector 256 is connected to junctions 210 and 215. A diode 260 is connected between junctions 215 and 217, and poled to be conductive toward junction 215. Output leads to amplifier 24 (FIG. 2) are provided at 261 and 262 in FIG. 3 from junctions 210 and 211, respectively. A transistor 263 is provided having a collector 264, an emitter 265 and a base 266. A resistor 267 is connected between junction 203 and an emitter 265. Collector 264 is connected to junction 211. Junctions 211 and 216 are connected together. Junctions 212, 213 and 214 are connected from base 266. A capacitor 268 is connected between junctions 204 and 212. A zener diode 269 is connected between junctions 205 and 213. A resistor 270 is connected between junctions 206 and 214.

An NPN transistor 271 is provided having a collector 272, an emitter 273 and a base 274. Pulse CH1 is applied to base 274 via a resistor 275. A resistor 276 is connected from collector 272 to junction 207. Emitter 273 is connected to junction 217.

Another transistor 277 is provided with a collector 278, an emitter 279 and a base 280. Pulse CH2 is supplied to base 280 via a resistor 281. A resistor 282 is connected from junction 214 to collector 278. Emitter 279 is connected to junction 221. A diode 283 is connected from junction 220 to junction 216 and poled to be conductive in a direction toward junction 216.

Pulse detector 30 may be as shown in FIG. 4. Differential amplifiers 38 and 39 in FIG. 4 are biased to provide high and low threshold detectors, respectively (see FIG. 5). The output of the circuit is shown at RX. Flip-flops 45 and 46 are a conventional integrated circuit (IC) pair model SN74LS112 sold by the Texas Instruments Company.

Figure 5:
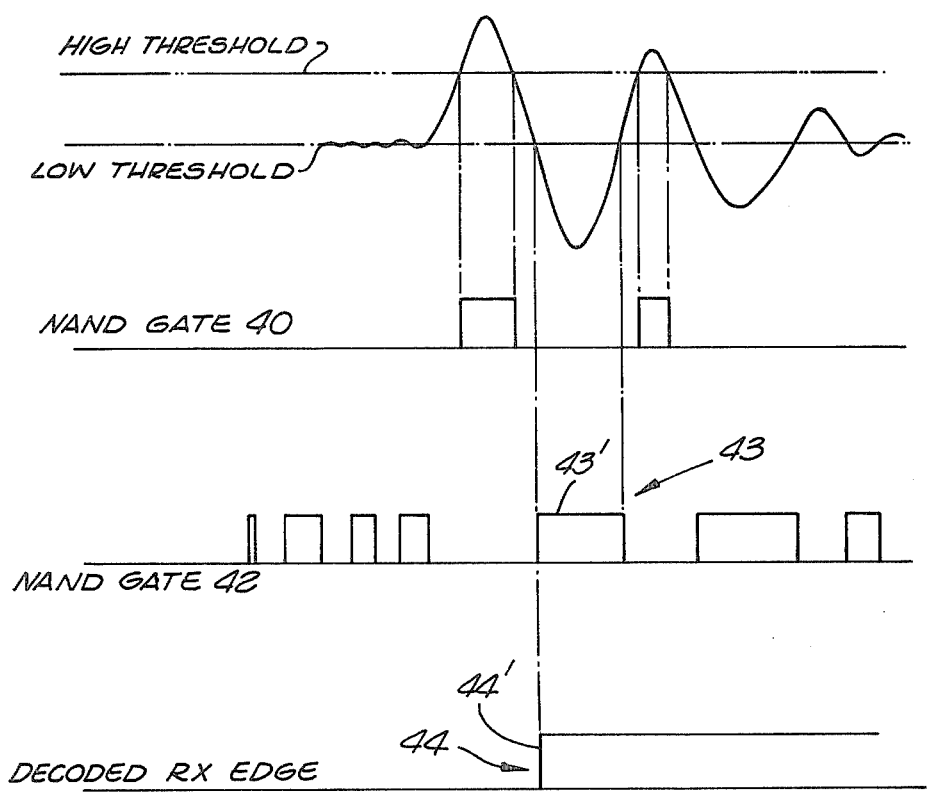
FIG. 5 is a graph of a group of waveforms characteristic of the operation of the pulse detector of FIG. 4.

The flip-flops 45 and 46 are low power Schottky flip-flops. These flip-flops, and the circuits connected thereto, are enabled by the logic $\overline{W1} + \overline{W2}$ (two "windows") so that the first high level of RX comparator output, shown at 41 (FIG. 5), i.e. in the output of NAND gate 40, sets flip-flop 45, enabling the second flip-flop 46. Flip-flop 46, in turn, is set by the "0" crossing output pulse 43' (FIG. 5). This produces the RX leading edge 44' which is fed to the edge or pulse comparator 31 (FIG. 6). By adjusting the "0" crossing threshold during $\overline{W1}$ or $\overline{W2}$, a small time delay can be added to or subtracted from the transit time, if desired, to provide an adjustment for zero change in frequency (range about ±30 nanoseconds).

In FIG. 4, junctions are provided at 284, 285, 286, 287, 288, 289, 290, 291, 292, 293, 294, 295, 296 and 297.

Resistors 298, 299 and 300 are provided. Resistor 298 is connected between junctions 287 and 290. Resistor 299 is connected between junctions 284 and 287. Resistor 300 is connected from junction 284 to, for example, ±5 volts. A capacitor 301 is connected between junctions 284 and 286. Junctions 286 and 287 are connected to, for example, ±2.5 volts.

Junction 284 is connected to the non-inverting input of amplifier 38. Junction 291 is connected to the inverting input of amplifier 38 and the noninverting input of amplifier 39.

Signal A6 is received by junctions 290 and 291.

NAND gate 40 receives one input from, for example, ±5 volts, one input from the output of amplifier 38, and one input from junction 288. NAND gate 42 receives an input from junction 288, a second input from the output of amplifier 39, and an input from the Q output of flip-flop 45.

Amplifiers 38 and 39 are differential amplifiers.

Switch 303 can change the received pulse threshold of RX2 from that of RX1. This can be employed to zero meter 37 (FIG. 2) or otherwise calibrate or align for component or subsystem or system irregularities.

Each of the NAND gates 40 and 42 receive $\overline{W1}+\overline{W2}$ pulses via junctions 296, 289 and 288, all three of which are connected together. The signals appearing on junctions 296 and 289 are respectively provided to the PR inputs of flip-flops 46 and 45.

The outputs of NAND gates 40 and 42 are respectively connected to the clock (CK) inputs of flip-flops 45 and 46. The output of NAND gate 40 is connected to a junction 285 which supplies a signal A1 to FIG. 12.

Each of the flip-flops 45 and 46 has a $\overline{Q}$ output connected to the respective J input thereof. The $\overline{Q}$ output and the J input of flip-flop 46 are connected to the junction 295 which carries an output signal A2.

The K inputs to the flip-flops 45 and 46 are connected to a junction 292 and thence to, for example, 0 volts.

The clear (CLR) inputs of flip-flops 45 and 46 are connected together at a junction 302 which may be maintained at, for example, +5 volts.

A W2 input operates switch 303 over lead 304. Switch 303 may be an electronic switch connected from +2.5 volts to junction 294.

Junctions 293 and 294 are connected together and to the inverting input of amplifier 39. A capacitor 305 is connected between junctions 293 and 297, junction 297 being maintained at, for example, 0 volts. A potentiometer is provided at 306 having a winding 307 and a wiper 308. Wiper 308 is connected to junction 293. A resistor 309 is connected from one end of winding 307 to, for example, +5 volts. A resistor 310 is connected from the other end of the winding 307 to junction 297.

In FIG. 6, pulses synchronous with the outputs of both VCO's 33 and 34 shown in FIG. 2 are applied as indicated at TR on an input lead (TR=TR1+TR2). "TR" means VCO synchronous pulses which the phase locked loops drive received pulses "RX" into coincidence. Flip-flops 47 and 48 are provided. These flip-flops may be conventional and of the type having a model number MC14013B and made by the Texas Instruments Company. NOR gates 49 and 50 are provided to close electronic switches 51 and 52.

Pulse comparator 31 is fed with transmit reference edge RX (44' in FIG. 5), and the function of the system is to bring the TR and RX edges (there is one pair for each VCO 33 and 34, namely TR1, RX1, and TR2, RX2) into coincidence. Each VCO 33 and 34 is thus employed in an electronic servo or phase locked loop, each of which has a path, a portion of each of which is common.

As will be explained hereinafter, capacitor 53 in FIG. 6 is charged and/or discharged by circuit 32 (FIG. 7) to be described. In FIG. 7 the voltages of capacitors 54 and 55 determine the respective frequencies F1 and F2 of VCO's 33 and 34, respectively. The voltages of capacitors 54 and 55 are updated in the following manner.

At the beginning of the time shared update for F1, switch Aa' closes charging capacitor 53 (FIG. 6) to the voltage of capacitor 54. Pulse comparator 31 (FIG. 6) then charges or discharges (partially or fully) capacitor 53 depending upon the error, if any, of time coincidence of the TR1 and RX1 pulses. Capacitor 53 (FIG. 6) then, through switch 105 (FIG. 7) via A4, charges or discharges capacitor 54. During the time shared F2 update, the same charging and discharging takes place in an identical manner between capacitor 55 (FIG. 7) and the selfsame capacitor 53 (FIG. 6).

The logic of NOR gates 49 and 50 in FIG. 6 is such that switch 51 will close and charge capacitor 53 for the time between the corresponding two pulses TR and RX when RX precedes TR. This raises the frequency of the corresponding VCO. On the other hand, if TR occurs before RX, switch 52 is closed. This lowers the frequency of the corresponding VCO.

In FIG. 6, junctions are shown at 311, 312, 313, 314, 315, 316, 317, 318, 319, 320, 321, 322, 323 and 324.

TR pulses are impressed upon the S signal input of flip-flop 47 via junction 311. A resistor 325 is connected from, for example, +5 volts to junction 311. The D inputs to flip-flops 47 and 48 are connected to, for example, +5 volts through junction 312. The S set inputs of flip-flops 47 and 48 are connected to, for example, 0 volts through junction 318. The reset inputs of flip-flops 47 and 48 are connected to $\overline{P1}+\overline{P2}$ via junction 324.

The S signal input of flip-flop 48 is RX through a junction 326. A resistor 327 is connected from, for example, +5 volts to junction 326. Signal A3 is taken from junction 326 on a lead 328.

NOR gate 49 has one input from the Q output of flip-flop 47 through junction 313, and another input from the $\overline{Q}$ output of flip-flop 48. A capacitor 329 is connected from junction 313 to, for example, 0 volts. Similarly, a capacitor 330 is connected from junction 319 to, for example, 0 volts. Capacitors 319 and 329 eliminate a dead band if Q to $\overline{Q}$ is an inverter causing a delay internal of each of flip-flops 47 and 48.

NOR gate 50 has one input from the $\overline{Q}$ output of flip-flop 47. NOR gate 50 has a second input from the Q output of flip-flop 48 via junction 319.

Electronic switch 51 is connected between junctions 314 and 316. Electronic switch 52 is connected between junctions 316 and 320. A resistor 331 is connected from junction 314 to +5 volts. Junctions 314 and 315 are connected together. A resistor 332 and a capacitor 333 are connected in parallel between junctions 315 and 317. Junction 317 may be maintained at 0 volts.

A resistor 334 is connected from junction 321 to +5 volts. Junctions 320 and 321 are connected together. A resistor 335 is connected between junctions 320 and 322. Junction 322 may be maintained at 0 volts. Junctions 322 and 323 are connected together. A capacitor 336 is connected between junctions 321 and 323. Capacitor 53 is connected between junctions 56 and 323. A resistor 332' is connected between junctions 316 and 56.

Resistors 331 and 335 have resistances much smaller than those of resistors 332 and 334, respectively.

In FIG. 7, pulse P1 occurs before pulse TF1, both of which occur before or after pulses P2 and TF2. Pulse P2 occurs before pulse TF2. See FIG. 13.

In FIG. 7, junctions are provided at 337, 338, 339, 340, 341, 342, 343, 344, 345, 346, 347, 348, 349, 350, 351 and 352. Other switches are provided at 353 and 354. All of the switches Aa', 105, 353 and 354 may be conventional electronic switches which are operated respectively by P1, TF1, P2 and TF2.

Switch Aa' is connected between junctions 337 and 57. The voltage at junction 57 is established by amplifier 58 or capacitor 53 in FIG. 6 at A4.

Amplifier 58 has a non-inverting input connected from junction 339, and an inverting input connected from junction 338. The output of amplifier 58 is connected to the input of VCO 33 via junctions 337 and 338. The inverting input of amplifier 58 is connected from junction 338.

Switch 105 is connected between junctions 339 and 340. Switch 353 is connected between junctions 334 and 345. Switch 354 is connected between junctions 349 and 345. Capacitor 54 is connected between junctions 339 and 343. Junction 343 is connected to 0 volts. Junctions 338 and 341 are connected together. Junctions 342 and 343 are connected together. A resistor 355 and a capacitor 356 are connected in parallel between junctions 341 and 342.

The non-inverting input of amplifier 59 is connected from junction 348. It is one feature of the present invention that the amplifiers 58 and 59 are unity gain differential amplifiers. The output of amplifier 59 is connected to the input of VCO 34 through junctions 344, 347 and 346, junction 346 also being connected to the inverting input of amplifier 59.

Junctions 347, 348, 359 and 350 are connected together. A resistor 357 and a capacitor 358 are connected in parallel between junctions 350 and 352. Junction 352 is connected to junction 351. Junction 351 is maintained at 0 volts. Capacitor 55 is connected between junctions 348 and 351.

Figure 8:
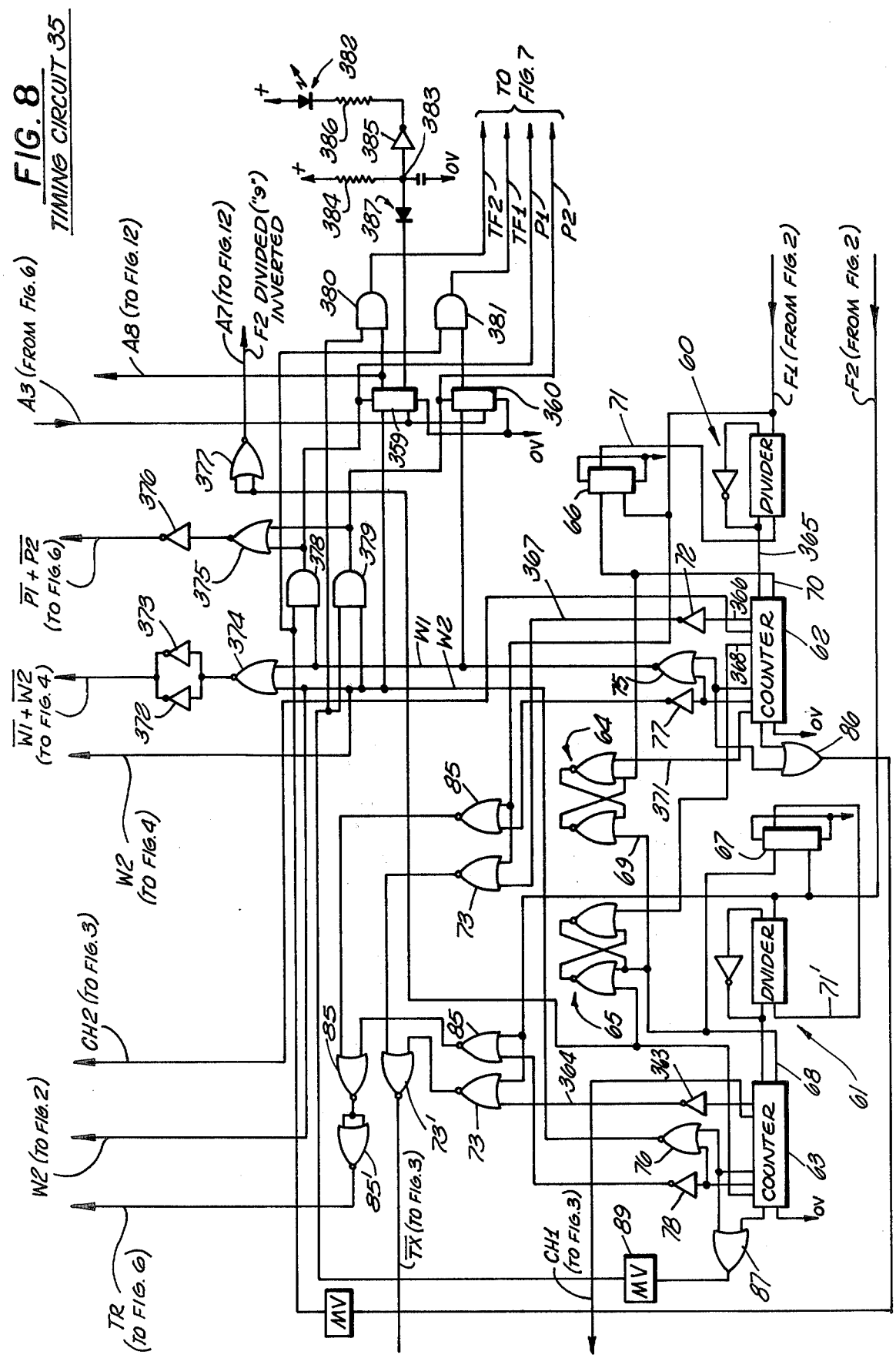
FIG. 8 is a schematic diagram of a timing circuit shown in FIG. 2.

As shown in FIGS. 2 and 8, VCO's 33 and 34 respectively have outputs F1 and F2. It is an outstanding feature of the present invention, in order to use a partial common path to minimize error, and yet to provide rapid updating for both of the VCO's 33 and 34, that the timing circuit 35 shown in FIG. 8 alternately compares TR and RX pulses for a VCO correction wherein transducer transmission occurs upstream and downstream consecutively.

Not only is the foregoing an outstanding feature of the present invention, it is also outstanding because the outputs of the VCO's 33 and 34 are asynchronous yet are used partially simultaneously.

The updating of the VCO frequencies is provided in spite of the asynchronous character of the frequencies because counters are employed, the count of one of which is picked up during the other and the other picked up after the reset of the one.

Manually adjustable dividers are provided at 60 and 61 (FIG. 8) for inputs F1 and F2. Counters are provided at 62 and 63 for the outputs of dividers 60 and 61, respectively.

Components 64 and 65 (Motorola MC14001B) form a quad 2-input NOR gate. These with "0" flip-flops 66 and 67 make it possible to cycle, for VCO frequency correction, first a phase locked loop including VCO 33 and then a phase locked loop including VCO 34. Dividers 60 and 61 may be identical and of the type manufactured and sold by Texas Instruments under the model number MC14516B.

Counters 62 and 63 may be identical and of the type sold by Texas Instruments Company under the model number MC14017B.

In FIG. 8, flip-flops 359, 360, 66 and 67 may all be identical and conventional. All four of these flip-flops may be identical to flip-flops 47 and 48 in FIG. 6. They may be each of the type MC1403B (Motorola).

Divider 60 may be identical to divider 61, and both may be conventional. Divider 60 is shown in FIG. 9. The numbers outside the rectangle 361 are the pin numbers. A set of switches independently actuable is illustrated at 362. The same switches 362 may be employed to set both dividers 60 and 61 (FIG. 8) at the same time. Dividers 60 and 61 are employed to divide the F1 and F2 inputs. Each divider 60 and 61 will divide by one of the numbers 1, 2, 4, 8 and 16 depending upon the setting of the switches in set 362 (FIG. 9).

Again, in FIG. 8, the TX2 (transmit) pulse will appear on the output lead 364 of an inverter 363 connected from the "1" output of counter 63.

To review, the output lead of divider 60 is shown at 365. This same lead provides the input or clock pulses to counter 62.

The "1" output of counter 62 is connected as the TX1 (transmit) pulse over lead 367 through inverter 72. Lead 368 is connected from the "3" output of counter 62. Leads 369, 370 and 371 are respectively connected from the "7," "8," and "9" outputs of counter 62.

The output leads of counter 63 are connected in an identical manner as those of counter 62 except that counter 63 has nothing connected to the "3" output lead thereof. Counter 63 starts on the count of "3" of counter 62. Counter 62 starts on the count of "9" of counter 63. See FIG. 13.

Parallel inverters are provided at 372 and 373 fed by a NOR gate 374.

A NOR gate 375 is also connected to another inverter 376. An inverter is again provided at 377. AND gates are provided at 378, 379, 380 and 381.

A loss of lock may be indicated by a light-emitting diode 382. From a junction 383 a resistor 384 is connected to a positive source of potential. An inverter 385, a resistor 386 and diode 382 are connected in series in that order from junction 383 to a positive source of potential. A diode 387 is connected from the Q output of flip-flop 359 to junction 383 and poled to be conductive away from junction 383. A capacitor 388 is connected from junction 383 to 0 volts.

A comparison of FIGS. 10 and 11 will show that counters 62 and 63 are connected in the same way except that counter 62 has a "3" output 389, and counter 63 in FIG. 11 does not.

As shown in FIGS. 10 and 11, counters 62 and 63 have reset input pins 15', clock pins 14' and output pins from 1 to 9 (not 0), pin 2 for the "1" output, pin 4 for the "2" output, etc. The "0" pin is not employed in either of the counters 62 or 63.

The AGC circuit 36 of FIG. 12 operates by deciding which of three possible events has taken place during a cycle.

These are:

(i) Normal signal received, no action;
(ii) Signal too large, increase AGC voltage;
(iii) Signal too small, decrease AGC voltage. The circuit of FIG. 12 decides which of the above has happened by gating certain signals.

NOR gate 79, inverters 79''' and 79'''', and NOR gate 79'' decide whether or not the received signal is too great in amplitude and NOR gate 80 if it is too small.

The signal is deemed too large if more than the first peak crosses the threshold set at the inverting input of differential amplifier 38 in FIG. 4. In this case one input to the NOR gate 79 monitors the output of flip-flop 46 for a received signal RX. This also gates out the first positive peak. The other input monitors the output of NAND gate 40 which produces logic '0' while the signal at the inverting input of 39 is above the level at the noninverting input of 38.

If after RX has gone to logic '0' the signal is large enough to produce more logic '0's at the output of 40, the output of 79 (FIG. 12) produces logic '1' pulses at 81. This turns on 81 in short bursts and charges 84. This increases the AGC voltage and attenuates the signal accordingly, until there are no more pulses at the output of NAND gate 40 (FIG. 4) after the first peak.

NOR gate 80 decides whether or not the signal amplitude is too low. It does this by monitoring the Q output of flip-flop 359 (FIG. 8). This point goes high if a signal has been received and stays low if not.

If the signal amplitude is too low, flip-flop 359 is not set and A8 (FIG. 8) is low at the end of window W2. This generates a short (200–400 ns) pulse that is inverted and applied to NOR gate 80 as a low '0' pulse. As the flip-flop 359 is not set and the other input to NOR 80 is at '0' the output pulses cause a logic '1' at 81 turning it on for a short time and thus discharging 84 causing a decrease in the AGC voltage and a decrease in signal attenuation.

Resistors connected from 81 and 82 control the amount of charge put into or taken from 84. If the input signal is of the correct amplitude neither of the outputs of NOR 79 nor NOR 80 are generated and the AGC voltage remains constant.

The voltage on 84 is buffered by amplifier 83 to provide a low impedance output.

The signal amplitude is reduced on both RX1 and RX2 but only increased by RX2. This is because it is required to decrease the amplitude faster than increase it because of the possibility of locking on noise.

By using the output of NAND gate 40 (FIG. 4) the amount of attenuation applied in one cycle is proportional to the size of the signal received.

In FIG. 12, junctions are provided at 390, 391, 392, 393 and 394.

Electronic switch 81 and a resistor 395 are connected in series in that order from junction 390 to +5 volts. Electronic switch 82 and a resistor 396 are connected in series in that order from junction 390 to 0 volts. Capacitor 84 is connected from junction 391 to 0 volts. A resistor 397 is connected from junction 393 to 0 volts. A capacitor 398 is connected from junction 394 to 0 volts.

Junctions 390 and 391 are connected to the noninverting input of differential amplifier 83. The inverting input is connected from the output of the amplifier 83 at junction 392 through a resistor 392'. Junctions 392, 393 and 394 are connected together.

In FIG. 12, a resistor 391' is connected from 0 volts to the inverting input of amplifier 83.

Figure 13:
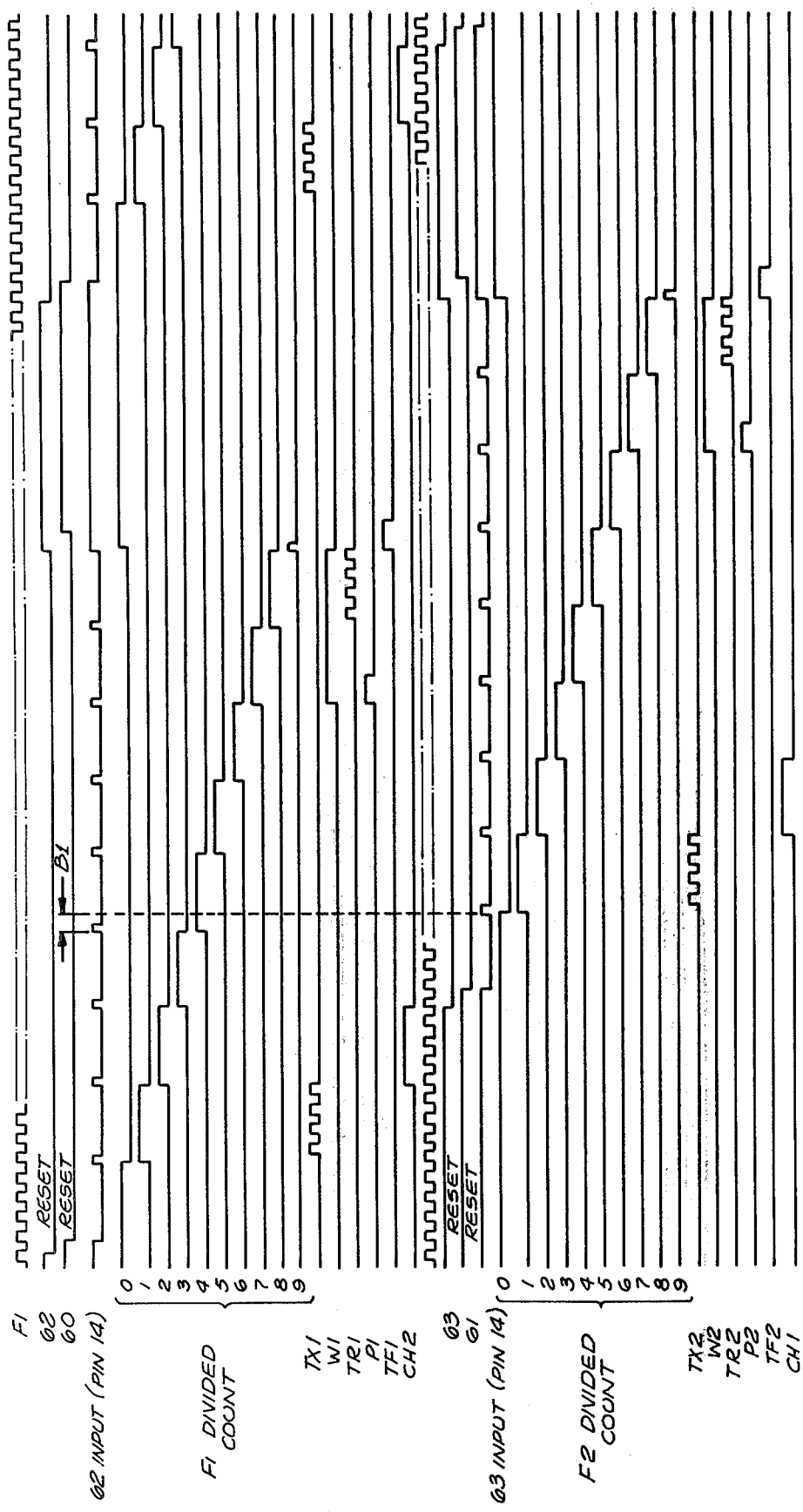
FIG. 13 is a graph of a group of waveforms characteristic of the operation of the present invention.

As shown in the waveforms of FIG. 13, the "9" output of counter 63 is a short pulse which is connected to flip-flop 65 (FIG. 8). This short pulse changes the state of flip-flop 65, and resets and disables a clock input to divider 61 and counter 63 via lead 68 and flip-flop 67. The flip-flops 64 and 66 form a latch that starts the count of divider 60 and counter 62. Counter 62 then transmits (TX1—FIG. 13) on the count of "1" of counter 62 via inverter 72 connected to a transmit NOR gate 73. It is an outstanding feature of the invention that pulses are transmitted in opposite directions at different times and are in flight simultaneously. The frequencies F1 and F2 are thus rapidly updated alternately.

Flip-flops 66 and 67 have F1 and F2 inputs, respectively, so that dividers 60 and 61 cannot consecutively begin to count except on the next succeeding corresponding F pulse after the corresponding D input changes to signal the beginning of the count.

Pulse CH2 is produced from the "2" output of counter 62 (FIG. 8). On the "3" count of counter 62, divider 61 and counter 63 are permitted to count. The count is picked up synchronously with F2, but asynchronously with F1. See dimension B1 in FIG. 13.

In FIG. 8, a NOR gate is provided at 75 which receives the "7" and "8" outputs of counter 62 to provide a window pulse W1 to block noise for received pulse RX1.

Similarly, a window pulse W2 is provided by a NOR gate 76 connected from counter 63. The windows are labeled W1 and W2, respectively, in FIG. 13.

TR1 and TR2 pulses are provided on the count of "8" of the counters 62 and 63, respectively, at inverters 77 and 78, respectively.

The transmitted and received pulses occur in the order of TX1, TX2, RX1, RX2.

OPERATION

The first waveform in FIG. 13 is F1. The second is the reset input of counter 62. The third is the reset of divider 60 (pin 9). Both resets are produced on or following the "9" count of counter 63 asynchronously with F2. However, counter 62 can begin to count at the next output of divider 60 and there is no inaccuracy. The fourth waveform in FIG. 13 is the clock input of counter 62. The next 10 are the 0 through 9 counts of counter 62. CH2 (synchronous with F1) is on the next line. Note in FIG. 8 the "3" count pin of counter 62 is connected to flip-flop 65 to cause counter 63 to begin to count. See the transmitted pulse TX2 later than TX1. Received pulses are compared with TR1 and TR2. W1 and W2 are "windows" which surround received pulses RX1 and RX2, respectively, and reduce noise.

In FIG. 1 the time $T_2$ it takes a pulse to travel from transducer 21 to transducer 22, for example, may be $$T_2 = s/(V_s + V_f \cos \theta) \quad (1)$$

where $V_s$ is the acoustical velocity, and
$V_f$ is the flowrate in unit length per unit time.
In the upstream direction the pulse transit time $T_1$ is
$$T_1 s/(V_s - V_f \cos \theta) \quad (2)$$

In accordance with the present invention, an electronic servo causes an integral number of VCO cycles to occur during a corresponding transit time. Thus, F1 is proportional to the reciprocal of $T_2$ or $T_1$. For example $$F1 = K/T_1 \quad (3)$$

and $F2 = K/T_2$ (4)

where K is an integer.
Thus, $$V_f = s\Delta f/(2K \cos \theta) \quad (5)$$

where $\Delta f = F2 - F1$. Typically F2 may be 283 KHz and F1 may be 280 KHz, both at 281.500 KHz at zero flow. $V_f$ may be read from frequency meter 37 in FIG. 2 ($\Delta f$), calibrated in rate of flow.

The "3" count of counter 62 resets counter 63 and divider 61 in FIGS. 8 and 13. The "9" count of counter 63 then resets divider 60 and counter 62.

No counter or divider counts or divides except upon reset. Flip-flop 65 resets 63 on the 62 count of "3". Flip-flop 64 terminates counter 62 on the "9" count thereof. Flip-flop 64 then resets 62 on the "9" count of 63.

NOR gates 85 provide TR outputs at gate 85'. NOR gates 73 provide TX pulses at gate 73'.

OR gates 86 and 87 are respectively connected to multivibrators 88 and 89. OR gate 86 is connected from the count "7" and clock enable pin 13 of counter 62. OR gate 87 is similarly connected. The output of multivibrator 88 eventually produces P1 and TF1. The output of multivibrator 89 eventually produces P2 and TF2.

The transducers may be conventional crystal transducers and each may charge up like a capacitor on CH1 and CH2 pulses. CH1 charges transducer 21 (FIG. 3) from which TX1 pulses only are transmitted. CH2 charges transducer 22 similarly. Pulse transmission occurs when the TX pulses discharge respective transducers.

The basic system operation relies on two phase locked loops, a portion of each path being common. This reduces chance for error. The phase locked loops are closed loop oscillators that run at frequencies corresponding to the appropriate propagation time across the fluid path. The term "lock" means that the control function has arrived at a stable condition where the input "error" (i.e. the small time difference between $T_R$ and $R_X$ edges) can cause a small modification of a VCO frequency that tends to reduce the error. With a modest gain, the error can be negligible. There is a dynamic situation, however, and this allows each VCO frequency to follow the fluctuation in flow.

If, for some reason, the flow is changed too rapidly—unlikely in practice—or the signal is lost because of foreign body in the ultrasonic path, then a situation arises where the system no longer has two valid inputs and consequently has no information on which to update itself. A coast-through feature of the present invention is provided to maintain the status quo during such an interruption.

The coast-through function is performed (in addition to rapid correction) by charging capacitor 53 (FIG. 6) alternately by unity gain voltage amplifiers 58 and 59 on pulses P1 and P2 (FIG. 7), respectively. If the charge of capacitor 53 does not change during operation of switches 51 and 52 (FIG. 6), the capacitors 54 and 55 (FIG. 7) have unchanged voltages.

The counters 62 and 63 are clocked through a complete cycle from zero through the nine stages to zero again where they are held by the reset, until released.

Similarly, the dividers 60 and 61 produce one output pulse for each "n" pulse—the preset value "n" being dependent on pipe diameter. Reset stops the counter, and holds it off.

Assuming F1 has just started counting and proceeds through its sequence, the following occurs.

When the leading edge of the first F1 (divided) pulse to cause counter 62 (FIG. 8) to count arrives after the reset has gone low, the "0" output goes high. Then the "1" of counter 62 occurs on the next F1 (divided). This enables the TX1 transmit pulse to discharge transducer 21. The next clock edge "2" of counter 62 then goes high and switches on the charging circuit 233 (FIG. 3) for transducer 22 and charges it to, for example, 80 volts.

On the next clock edge to counter 62, "3" goes high. This resets the latch formed by 64, 65, 66 and 67 (FIG. 8). This removes the reset on counter 63 and precisely on the second positive clock edge of F2, the output of flip-flop 67 causes divider 61 to divide at 71', removing the reset on divider 61 in the previous one.

Divider 61 and counter 63 are both enabled and now proceed through their timing.

The next three clock pulses to counter 63 cause "0", "1" and "2" thereof to go high in succession as before.

The next clock pulse to counter 62 (the seventh from the start) causes the "7" output of counter 62 to go high, which starts the window W1 (FIG. 13) and enables flip-flops 45 and 46 (FIG. 4) and multivibrator 88 (FIG. 8), causing a small pulse. This is gated at 378 with the window W1 and becomes P1 which switches on the analog gate Aa' (FIG. 7) and restores capacitor 53 to the voltage of capacitor 54. Flip-flops 47 and 48 are reset by $\overline{P1}+\overline{P2}$ (FIG. 6).

The next clock pulse to counter 62 causes its output "8" to go high. This generates a TR1 pulse to flip-flop 47 (FIG. 6) and keeps flip-flops 45 and 46 (FIG. 4) enabled.

The next clock pulse to counter 62 causes the "9" output thereof to go high. This sets the latch 64 etc., instantly resetting counters 62 and 63, and on the next clock edge of F1 resets divider 60.

Pin 12 (FIG. 10) of counter 62 (FIG. 8) produces a pulse through OR gate 86 when it is reset which triggers multivibrator 88, causing another pulse. This, when gated with W1 and W2 to provide TF1 (379, 360 and 381), causes capacitor 54 to charge or discharge from capacitor 53 (FIGS. 7 and 6).

Counting of counter 62 is now stopped and window W1 closed with 47, 48 (FIG. 6) disabled. Compare the pin 14 of counter 62 waveform in FIG. 13 (large pulse) with the trailing edge of the W1 pulse.

Note in FIG. 13 that F1 and F2 are asynchronous. Divider 60 begins to count F1 on the first edge of the next F1 pulse after or on the reset of counter 61. The reverse is not true because the normal sequence is TX1, TX2, RX1, RX2, TX1 etc.

For changeover from divider 60 to divider 61, counter 61 counts the first edge of F2 after or on the trailing edge of the "2" output of counter 62.

Counters 61 and 63 having started, TX2 is produced at "1" and is transmitted from 73' (FIG. 8) to transducer 21.

On the next clock pulse to counter 63, "2" goes high. This produces charging pulse CH1.

The next three clock pulses cause "3", "4", "5" and "6" to go high in turn.

The next clock pulse to counter 63, the seventh from the removal of the reset, causes "7" to go high, this opens window W2 (FIG. 13), enabling 45, 46 (FIG. 4) again and triggering multivibrator 89. This pulse is gated with window W2 and becomes P2 which resets 47, 48 (FIG. 6) and opens the transmission gate equalizing the voltages of capacitors 53 and 55 (FIGS. 6 and 7).

On the next clock to counter 63, "8" goes high. "8" continues W2 and enables the generation of TR2 which clocks 47, 48 (FIG. 6).

The next clock pulse causes "9" to go high.

"9" sets the latch which resets counter 63 and resets the latch on the next clock to counter 63 from VCO 33. Then, counter 63 is reset.

Multivibrator (one shot) 89 is triggered again and generates TF2 which performs the same function for capacitor 55 as TF1 did for capacitor 54.

Latch 64 being reset by latch 65 removes the reset from divider 60 and from counter 62 by VCO 33. Thus counter 62 and divider 60 can now count.

Counter 62 initiates the reset of itself and divider 60.
Counter 63 initiates the reset of itself and divider 61.

Thus each counter pair reset themselves but enable the other, the enable being synchronized with the clock (F1 or F2) of the one being enabled or the next clock edge thereof received. Note F1 is connected to the S input of flip-flop 66 and F2 is connected to the S input of flip-flop 67.

Many of the components disclosed in the drawings are, per se, old in the art and many may be purchased as integrated circuits or semiconductors or the like. The following are typical.

|  | Component | Integrated Circuit |
|---|---|---|
| FIG. 2 | Electronic Attenuator 28 | MC3340P (Motorola) |
|  | VCO 33 | MC14046B (Motorola) |
|  | VCO 34 | MC14046B (Motorola) |
| FIG. 4 | Amplifiers 38 and 39 and NAND gates 40 and 42 (one chip) | DS75207 (National) |
|  | Flip-flops 45 and 46 (one chip) | SN74LS112 (Texas Instruments) |
| FIG. 6 | Flip-flops 47 and 48 (one chip) | MC4013B (Motorola) |
| FIG. 8 | Dividers 60 and 61 (two chips) | MC14516B (Motorola) |
|  | Counters 62 and 63 (two chips) | MC4017B (Motorola) |
|  | Flip-flops 64 and 65 (one chip) | MC14001B (Motorola) |
|  | Flip-flops 66 and 67 (and window flip-flops) (one chip each pair) | MC14013B (Motorola) |
|  | Multivibrators 88 and 89 (one chip) | MC14528B (Motorola) |

In FIG. 13, F1 and F2 are the respective outputs of VCO's 33 and 34. Upper 62 and 63 are the reset outputs of counters 62 and 63, respectively. Numbers 60 and 61 are the reset inputs of dividers 60 and 61, respectively. The 62 and 63 inputs to respective pins 14 of counters 62 and 63 are the clock inputs thereto (F1 and F2 divided by dividers 60 and 61, respectively).

The upper and lower sets of digits 0, 1, 2, 3 . . . 9 are the amplitudes of the "0", "1", "2", "3" . . . "9" outputs of counters 63 and 62, respectively.

TX1 and TX2 are transmit pulses for transducers 21 and 22, respectively. W1 and W2 are the windows for pulses received by transducers 22 and 21, respectively. TR1 and TR2 are synchronous with F1 and F2, respectively, and appear first at the "8" outputs of counters 62 and 63, respectively (FIG. 8). They are used in pulse comparator 31. See FIGS. 2 and 6. P1 and TF1 are synchronous with F1. P2 and TF2 are synchronous with F2. P1, P2, TF1 and TF2 operate the switches of charge storage circuit 32 of FIG. 7.

What is claimed is:

1. A flowmeter comprising: a first transducer for mounting at a first point in a pipeline; a second transducer for mounting in alignment with said first transducer, but at a second point in said pipeline spaced lengthwise from said first point; first means including first and second voltage controlled oscillators to energize respectively said first and second transducers at first and second respective times to propagate pulses through fluid in said pipeline; second means to receive pulses transmitted from said first and second transducers through said fluid and subsequently through said second and first transducers, respectively; a first threshold detector of one polarity and of a first threshold level connected from said second means; a first storage device; a second storage device having an output lead, said first storage device being adapted to enable and to disable said second storage device, said first storage device being connected from said first threshold detector to enable said second storage device when said first threshold level is exceeded; a second threshold detector of a polarity opposite said one polarity and of a second threshold level connected from said second means to said second storage device to transmit a received pulse from said second storage device on said output lead thereof when said second threshold level is reached, but only after said first storage device has enabled said second storage device; third means operable synchronously with said first means to reset said first and second storage devices; and fourth means connected from said second storage device output lead to said first and second voltage controlled oscillators to maintain the difference between the output frequencies of said first and second voltage controlled oscillators directly proportional to one condition of a fluid in the pipeline.

2. The invention as defined in claim 1, wherein said condition is the volume rate of flow of fluid in said pipeline.

3. A flowmeter comprising: a first transducer for mounting at a first point in a pipeline; a second transducer for mounting in alignment with said first transducer, but at a second point in said pipeline spaced lengthwise from said first point; first means including first and second voltage controlled oscillators to energize respectively said first and second transducers at first and second respective times with first and second pulses to transmit vibrations through fluid in said pipeline in opposite directions, respectively; second means to receive vibrations transmitted from said first and second transducers through said fluid and subsequently through said second and first transducers, respectively; a first counter adapted to count a plurality of pulses before reset, and connected from said first voltage controlled oscillator (VCO); a second counter adapted to count a plurality of pulses before reset, and connected from said second VCO; third means connected from said second means and said first and second counters to control the frequency of said first VCO and to control the frequency of said second VCO in a manner such that a first pulse, transmitted at a first time by said first transducer, arrives at said second transducer a second time later than said first time by an integral number of counts of said first counter, and in a manner such that a third pulse, transmitted at a third time by said second transducer, arrives at said first transducer a fourth time later than said third time by an integral number of counts of said second counter; fourth means responsive to one state of said second counter to gate the output of said first VCO to said first transducer; and fifth means responsive to one state of said first counter to gate the output of said second VCO to said second transducer.

4. The invention as defined in claim 3, wherein sixth means are provided which are connected from said first and second voltage controlled oscillators to maintain the difference between the output frequencies of said first and second voltage controlled oscillators directly proportional to one condition of the fluid in said pipeline.

5. The invention as defined in claim 4, wherein said condition is the volume rate of flow of said fluid in said pipeline.

6. A flowmeter comprising: a first transducer for mounting at a first point in a pipeline; a second transducer for mounting in alignment with said first transducer, but at a second point in said pipeline spaced lengthwise from said first point; first means including first and second voltage controlled oscillators to energize respectively said first and second transducers at first and second respective times to transmit vibrations through fluid in said pipeline in opposite directions; second means to receive vibrations transmitted from said first and second transducers through said fluid and subsequently through said second and first transducers, respectively; a time shared comparator having an output capacitor and third means to charge and to discharge said output capacitor when one received pulse arrives respectively after and before a corresponding pulse of the output of a voltage controlled oscillator (VCO) which caused the transmission of the pulse received; first and second storage capacitors to provide input control voltages to said first and second VCO's, respectively; and first and second switches connected from said output capacitor to said first and second storage capacitors, respectively; and fourth means connected from said first and second VCO's to operate each of said first and second switches momentarily, respectively, to modify the charge on said first and second storage capacitors when necessary to change the VCO frequencies such that the said received pulses occur after an integral number of pulses of a corresponding VCO.

7. The invention as defined in claim 6, wherein first and second unity gain voltage amplifiers are respectively connected from said first and second storage capacitors, and third and fourth switches are respectively connected from the outputs of said first and second amplifiers to said output capacitor, and fifth means connected from said VCO's to operate said third and fourth switches alternately and momentarily to charge said output capacitor before a received or corresponding pulse arrives to initial voltages equal to those of said first and second storage capacitors, said initial voltages minimizing the time required for correcting the charge on said output capacitor.

8. A compound phase locked loop for detecting a property of a fluid comprising: a first voltage controlled oscillator (VCO) having an input and an output; a second VCO having an input and an output; a first transducer; a second transducer, said first and second transducers each being adapted to transmit and to receive energy respectively to and from each other, the transit times of the propagation of energy from said first transducer to said second transducer and vice versa being a function of the acoustical velocity and volume rate of flow of a fluid located between said first and second transducers; logic means connected from the outputs of both of said VCO's to sequence operation, said logic means including first counter means connected from said first VCO to transmit first pulses only from said first transducer on a count of said first counter means, said logic means including second counter means connected from said second VCO to transmit second pulses from said second transducer on a count of said second counter means, but spaced in time from said first pulses and all received pulses; a common receiver to act upon pulses received by both of said transducers, said common receiver producing received pulse edges; a common pulse comparator connected from both of said VCO's and from said common receiver to receive pulse edges therefrom, said logic means including third means to supply pulse edges for comparison from said first and second counter means to said common pulse comparator; first and second electronic servo means connected from said common pulse comparator to said first and second VCO inputs, respectively, and actuable to cause a first alternate set of received pulse edges to lie in coincidence with edges corresponding to output pulses of said first counter means, and actuable to cause a second alternate set of said received pulse edges to lie in coincidence with edges corresponding to output pulses of said second counter means; and first and second switch means to connect said comparator to said VCO inputs alternately on a time shared basis.

9. A phase locked loop comprising: a voltage controlled oscillator (VCO) having an input and an output; a pulse comparator having first and second inputs and an output; means connected from said VCO output to transmit a pulse over a path which varies the propagation time, said transmitted pulse being received at the end of said path by said pulse comparator first input, said pulse comparator second input being connected from said VCO output, said comparator output being connected to said VCO input to act as an electronic servomechanism and to drive said VCO until the output thereof produces a predetermined number of integral cycles during the time period between the instant that said pulse is transmitted and the instant that it is received at said pulse comparator first input, said pulse comparator including a first capacitor to retain a voltage to drive said VCO, a second capacitor having a capacitance smaller than said first capacitor, first means actuable to charge said second capacitor periodically to the voltage of said first capacitor, second means actuable to charge or discharge said second capacitor depending upon the accuracy of the number and phase of said predetermined number of cycles, third means actuable to connect said first and second capacitors in parallel for equalizing the voltages thereon, and fourth means to actuate said first means, said second means, and said third means repeatedly in that order.

* * * * *